(12) United States Patent
Gartside et al.

(10) Patent No.: US 8,178,736 B2
(45) Date of Patent: May 15, 2012

(54) PROCESS AND SYSTEM FOR THE PRODUCTION OF ISOPRENE

(75) Inventors: Robert J Gartside, Summit, NJ (US); Shane R Kleindienst, Succasunna, NJ (US)

(73) Assignee: Lummus Technology Inc., Bloomfield, NJ (US)

(*) Notice: Subject to any disclaimer, the term of this patent is extended or adjusted under 35 U.S.C. 154(b) by 391 days.

(21) Appl. No.: 12/462,688

(22) Filed: Aug. 7, 2009

(65) Prior Publication Data

US 2011/0034747 A1 Feb. 10, 2011

(51) Int. Cl.
*C07C 6/04* (2006.01)
*C07C 4/10* (2006.01)
*C07C 5/25* (2006.01)

(52) U.S. Cl. ........ 585/324; 585/332; 585/643; 585/648; 585/664

(58) Field of Classification Search .......... 585/324, 585/332, 643, 664, 648
See application file for complete search history.

(56) References Cited

U.S. PATENT DOCUMENTS

| | | | |
|---|---|---|---|
| 3,284,532 A | 11/1966 | Frech | |
| 3,327,000 A | 6/1967 | Keith et al. | |
| 3,382,289 A | 5/1968 | Edwards et al. | |
| 3,595,280 A | 7/1971 | Fissel | |
| 3,646,143 A | 2/1972 | Ellis et al. | |
| 3,686,352 A | 8/1972 | Neal et al. | |
| 4,049,616 A | 9/1977 | Scott et al. | |
| 5,057,638 A | 10/1991 | Sweeney | |
| 5,057,644 A | 10/1991 | Lin et al. | |
| 5,304,692 A | 4/1994 | Yamada et al. | |
| 6,166,279 A | 12/2000 | Schwab et al. | |
| 6,538,168 B1 * | 3/2003 | Schwab et al. | 585/647 |
| 6,646,172 B1 * | 11/2003 | Schwab et al. | 585/324 |
| 6,875,901 B2 | 4/2005 | Gartside et al. | |
| 7,169,953 B2 | 1/2007 | Zhang et al. | |

FOREIGN PATENT DOCUMENTS

| | | | |
|---|---|---|---|
| CH | 478 072 A | 9/1969 | |
| GB | 832 475 A | 8/1960 | |
| GB | 934 450 A | 8/1963 | |

OTHER PUBLICATIONS

K. J. Frech et al., Factors Affecting Methyl Pentene Pyrolysis, ACS Symposium Series (pp. 197-217), 1976.
Robert L. Banks et al., Synthesis of Isoamylene via Olefin Disproportionation, Ind. Eng. Chem. Prod. Res. Develop., vol. 10, No. 1, 1071 (pp. 46-51), 1971.
International Search Report and Written Opinion of the International Searching Authority mailed May 2, 2011, for PCT/US2010/002115 filed Jul. 29, 2010.

* cited by examiner

*Primary Examiner* — Thuan Dinh Dang
(74) *Attorney, Agent, or Firm* — Alix, Yale & Ristas, LLP

(57) ABSTRACT

Disclosed herein is a process for producing isoprene that includes reacting a mixed $C_4$ metathesis feed stream comprising isobutylene and at least one of 1-butene and 2-pentene in a first metathesis reactor in the presence of a first metathesis catalyst under conditions sufficient to produce an intermediate product stream comprising at least 30 wt. % 2-methyl-2-pentene based upon the olefin content of fresh feed in the mixed $C_4$ feed stream, and at least one of ethylene and propylene, separating the 2-methyl-2-pentene, subjecting the separated 2-methyl-2-pentene to pyrolysis to produce a reaction product stream comprising isoprene, and separating the isoprene into an isoprene product stream using fractionation. A system used in producing isoprene is also disclosed.

16 Claims, 4 Drawing Sheets

US 8,178,736 B2

PROCESS AND SYSTEM FOR THE PRODUCTION OF ISOPRENE

BACKGROUND

The disclosed embodiments generally relate to the production of 2-methyl-2-pentene and isoprene and more particularly to the use of a mixed $C_4$ stream to produce 2-methyl-2-pentene, which subsequently is converted to isoprene.

2-methyl-2-pentene is a product found in steam cracking effluents at low concentrations. It is in the presence of many closely boiling $C_5$ and $C_6$ olefin isomers, making recovery at significant volumes difficult and expensive.

It is known from U.S. Pat. No. 6,538,168 to produce $C_5/C_6$ olefins from a stream of $C_4$ hydrocarbons. The initial metathesis reaction of the $C_4$ olefins produces a mixture of $C_2$-$C_6$ olefins and butanes. In one embodiment described in U.S. Pat. No. 6,538,168, the $C_2$-$C_6$ olefins mixture is fractionated in a multi-stage distillation process to give a low boiling fraction A containing $C_2$-$C_4$ olefins and butanes, or $C_2$-$C_3$ olefins, a higher but still low boiling fraction B containing butenes and butanes, an intermediate boiling fraction C containing pentene and methylbutene, and a high boiling fraction D containing hexene and methylpentene. In some cases, the $C_5$ and $C_6$ olefins are separated from one another by fractionation. In Example 3 described therein, the product stream contains 99.5% wt. 3-hexene. The 1-butene conversion rate is 91% wt. and the 2-butene conversion rate is 50% wt. Isobutylene is removed before metathesis so that the reactant stream for metathesis contains only 2.0% isobutylene. The concentration of 2 methyl 2-pentene in this case is low (<1%).

Other known processes produce 2-methyl-2-pentene from propylene. A process that involves dimerizing propylene to form methyl-pentenes and dimethyl-butenes is described in U.S. Pat. No. 3,686,352. However, when 2-methyl-2-pentene is formed using propylene as a reactant, feedstock costs are high.

Isoprene (2-methyl-1,3-butadiene) is a precursor to 1,4-polyisoprene, which is a synthetic version of natural rubber. Isoprene is conventionally recovered from the $C_5$ fraction of the effluent of steam cracking of naphtha or heavier oils. The steam cracker $C_5$ stream is sent to a solvent extraction process typically using acrylonitrile as the solvent. This route is complicated by the presence of cyclopentadiene that is also removed selectively by the solvent.

In the 1950's and 1960's, the Goodyear Tire and Rubber Company developed a process for converting 2-methyl-2-pentene to a range of hydrocarbons, mainly isoprene, methane, and isobutylene. The 2-methyl-2-pentene can be subsequently cracked in a pyrolysis reactor to form isoprene and other products, as is described in "Factors Affecting Methyl Pentene Pyrolysis", Frech et al, ACS Symposium Series, 1976). The products comprise methane, ethylene, butadiene, isoprene butenes, and $C_6$ dienes. The reaction takes place at temperatures of 600 Deg. C. or higher and under high dilution to avoid isoprene polymerization. The Goodyear process used HBr or a mixture of $H_2S$ and $NH_3$ as a homogeneous catalyst to promote selectivity of isoprene in a thermal cracking reaction. Goodyear tests with HBr showed single pass yields of 54.5% mol. isoprene from 2-methy-2-pentene. The isoprene then can be separated from this mixture by using extractive distillation. This work is discussed in Lloyd M. Elkin, *Isoprene*, Stanford Research Institute Process Economics Report No. 28 (p. 60), 1967.

An alternate isoprene production route is to dehydrogenate isoamylenes (methyl butenes). The dehydrogenation step has been practiced commercially by Air Products using their Catofin process. Isoamylenes typically have been recovered by steam cracking $C_5$ product streams. In those cases however, the process is complicated by the presence of cyclopentadiene. The $C_5$ product stream requires selective hydrogenation to remove the dienes that would rapidly foul a dehydrogenation catalyst. The dehydrogenation step is also very costly, requiring vacuum operation and significant capital expense. Isoamylenes can also be formed by the metathesis of butenes and propylene, as is described in Ind. & Eng. Chemistry Prod. Res. Develop., Vol. 10, No. 1, 1071 pg. 46). These isoamylenes can then be dehydrogenated to isoprene as above.

It would be useful to develop a process that results in a high yield of 2-methyl-2-pentene from mixed $C_4$ olefin streams, combined with high butenes conversion. The 2-methyl-2-pentene can then be used to produce isoprene.

SUMMARY

One embodiment is a process comprising reacting a mixed $C_4$ metathesis feed stream comprising isobutylene and at least one of 1-butene and 2-pentene in a first metathesis reactor in the presence of a first metathesis catalyst under conditions sufficient to produce an intermediate product stream comprising at least 30 wt. % 2-methyl-2-pentene based upon the olefin content of fresh feed in the mixed $C_4$ metathesis feed stream, and at least one of ethylene and propylene, separating the 2-methyl-2-pentene, subjecting the separated 2-methyl-2-pentene to pyrolysis to produce a reaction product stream comprising isoprene, and separating the isoprene into an isoprene product stream using fractionation.

Another embodiment is a process comprising reacting a mixed $C_4$ metathesis feed stream comprising isobutylene and 1-butene in the presence of a first metathesis catalyst under conditions sufficient to produce an intermediate product stream comprising 2-methyl-2-pentene and at least one of ethylene and propylene, fractionating the intermediate product stream to form a 2-methyl-2-pentene stream and at least one of an ethylene stream and a propylene stream, subjecting the separated 2-methyl-2-pentene stream to pyrolysis to produce a reaction product stream comprising isoprene, and separating the isoprene to form an isoprene product stream using fractionation.

A further embodiment is process comprising reacting a mixed $C_4$ metathesis feed stream comprising isobutylene and 2-pentene in the presence of a first metathesis catalyst under conditions sufficient to produce an intermediate product stream comprising propylene, 2-methyl-2-pentene, ethylene, 2,3-dimethyl-2-butene and 2-butene, separating the intermediate product stream in a multi-stage fractionation process to form a 2-methyl-2-pentene stream, a distillate stream containing ethylene and propylene, and a 2,3-dimethyl-2-butene stream, subjecting the separated 2-methyl-2-pentene stream to pyrolysis to produce a reaction product stream comprising isoprene, and separating the isoprene into an isoprene product stream using fractionation.

Yet another embodiment is a system comprising a first metathesis reactor, a second reactor, a first multistage fractionation system, a pyrolysis heater and a second multistage fractionation system. The first metathesis reactor is configured to react isobutylene with at least one of 1-butene and 2-pentene to produce 2-methyl-2-pentene. The second reactor comprises at least one of an isomerization reactor configured to isomerize 2-butene to form 1-butene, and a metathesis reactor configured to react 2-butene with at least one of ethylene and 1-butene to produce propylene. The first multistage fractionation system is configured to produce a 2-methyl-2- pentene stream and a 2,3-dimethyl-2-butene stream. The pyrolysis heater is configured to crack the 2-methyl-2-pentene to produce isoprene and other hydrocarbons. The second multistage fractionation system is configured to separate isoprene from the other hydrocarbons.

DETAILED DESCRIPTION

Figure 1:
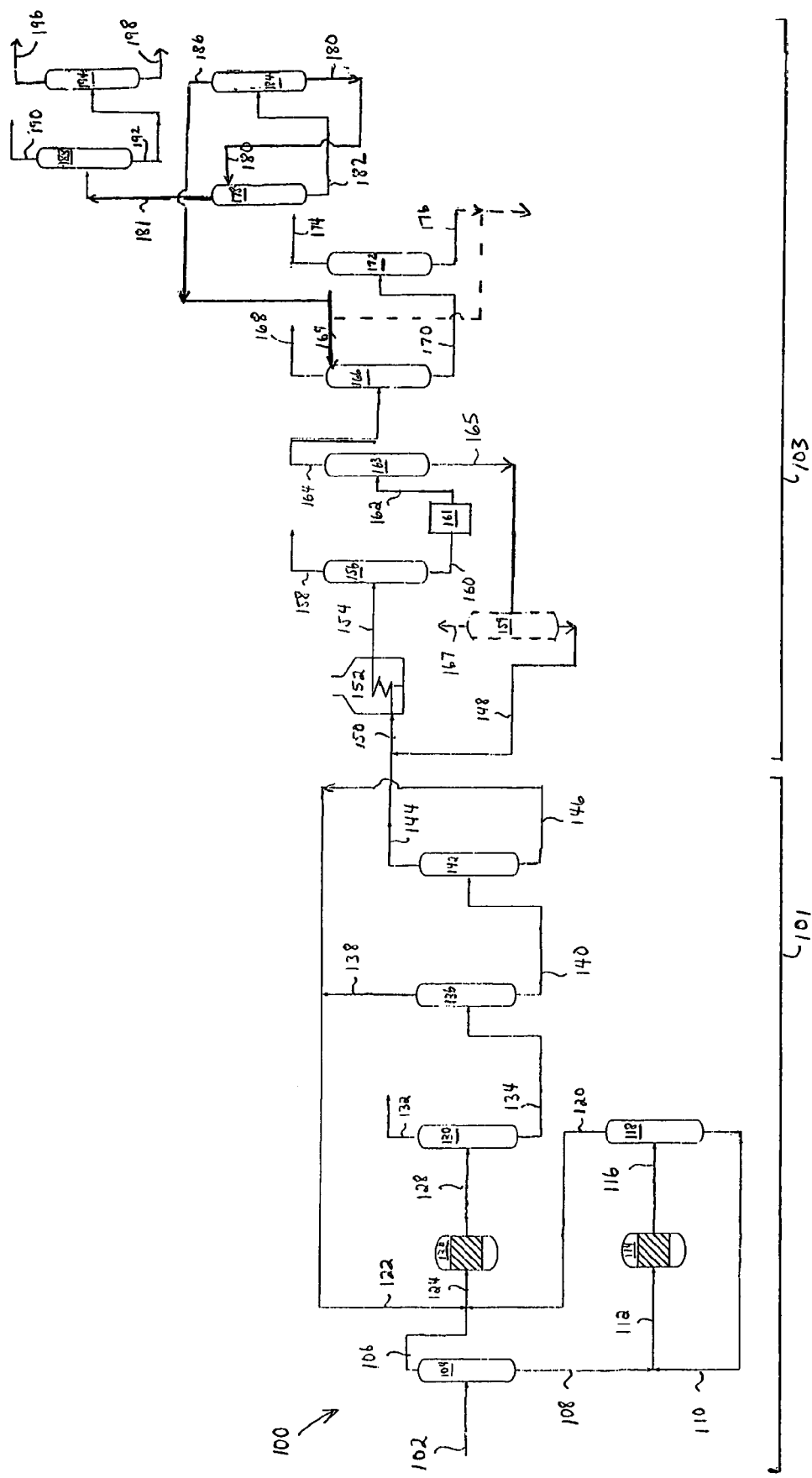
FIG. 1 is a flow sheet according to a first process and system described below.

Systems and processes are described herein for the efficient production of isoprene using isobutylene as a reactant. The processes enable production of an iso hexene material in high concentration without using expensive propylene as would be required for dimerization. The 2-methyl-2-pentene can then be used to produce isoprene utilizing the thermal cracking route, which is lower cost and higher in yield than catalytic dehydrogenation involving isoamylenes. In some embodiments, other valuable product streams are produced, including ethylene and propylene.

As used herein, "conversion" refers to the mol. % of reactant converted into product. "Actual yield" as used herein and in Table 1 refers to the actual mass or weight of product obtained (having subtracted the product losses due to purge streams and fractionation), divided by the predicted mass or weight of product if no competing reactions took place. Yield can be expressed as a percent, and is based on an overall material balance. As used herein, "selectivity" in Table 1 refers to the mass of a particular product compound formed, divided by the mass of all products formed, not including unconverted reactant, expressed as a percent. Selectivity is based on an overall material balance.

The processes described herein use isobutylene as a reactant in the metathesis reactor. In one embodiment, 2-butene is isomerized to 1-butene, which is then sent to the metathesis reactor where it is reacted with isobutylene to form ethylene and 2-methyl-2-pentene. In other cases, ethylene produced in the metathesis reaction of isobutylene and 1-butene is used in a metathesis reaction of 2-butene and ethylene to produce propylene as an additional product. In another embodiment, 1-butene and 2-butene are reacted in one metathesis reactor to form propylene and 2-pentene, and the 2-pentene is then reacted with isobutylene in another metathesis reactor to form 2-methyl-2-pentene. In each case, a set of distillation towers is used to obtain the desired product and recycle streams.

The metathesis catalyst may be any suitable metathesis catalyst including but not limited to oxides of Group VIB and Group VIIB metals on supports. Non-limiting examples include tungsten, molybdenum, and rhenium oxides. Catalyst supports can be of any type and could include alumina, silica, mixtures thereof, hydrotalcites, zirconia, and zeolites. In addition to the metathesis catalyst, the catalyst in the metathesis reactor can include a double bond isomerization catalyst such as magnesium oxide or calcium oxide. The metathesis reactions typically take place at a temperature between 50° and 450° C., preferably between 300° and 400° C.

A method for the double bond isomerization of 2-butene to form 1-butene is described in commonly assigned U.S. Pat. No. 6,875,901, the contents of which are incorporated herein by reference in their entirety. Non-limiting examples of catalysts used in the isomerization of 2-butene to 1-butene are basic metal oxide catalysts.

2-methyl-2-pentene produced in the metathesis reactions is converted to isoprene in a cracking process, followed by use of a solvent extraction or liquid adsorption system for the recovery of isoprene. In a typical process of this type, a pyrolysis process yields a full spectrum of products from methane gas, $C_2$, $C_3$, and $C_4$ hydrocarbons, $C_5$ hydrocarbons including isoprene, cyclopentadiene, methyl-butenes, and piperylenes, unconverted 2-methyl-2-pentene and other $C_6$ hydrocarbons, and heavies. The mixture is then quenched with a caustic solution. After water separation, the mixture is sent to a distillation/adsorption section where a $C_6+$ liquid is used to adsorb the $C_5$ material. Methane and some of the $C_4$ or lighter components are removed overhead. The bottoms ($C_6+$) flows to a fractionation step. The $C_5$'s (mainly isoprene) are then stripped from the heavy $C_6+$ liquid. Any cyclopentadiene has been dimerized to dicyclopentadiene and flows out the bottom of this stripping column. 2-methyl-2-pentene as the bottom stream from this second tower is then sent to a third tower where it is distilled overhead and recycled to the cracking furnace. The bottoms heavy liquid is recycled as the solvent. $C_5$ paraffins and mono-olefins including methyl-butenes from the stripping column overhead are separated in an extractive distillation column, with isoprene remaining in the solvent. Isoprene is separated from the solvent in a stripping column and is water washed to remove traces of the solvent. Crude isoprene is sent to a fractionation sequence in which alkynes are removed as the distillate in a first distillation tower and a second distillation tower removes piperylenes as a bottom stream and isoprene is collected as distillate. As would be evident to those skilled in the art, there are variations possible in the separation of isoprene from a cracking effluent and the above process is a non-limiting example.

Advantages of the processes described herein include the following:

1. 2-methyl-2-pentene is produced in high concentration from a $C_4$ stream. As mentioned above, conventional methods for production of 2-methyl-2-pentene from propylene result in a high cost feedstock since propylene is much more expensive than butenes.

propylene+propylene→2-methyl-2-pentene→isoprene+methane

In contrast, in certain embodiments described herein, 1-butene+isobutene→2-methyl-2-pentene+ethylene
    2-methyl-2-pentene→isoprene+methane
    2-pentene+isobutene→2-methyl-2-pentene+propylene
    2-methyl-2-pentene→isoprene+methane Thus, the process described herein uses mixed $C_4$s to produce 2-methyl-2-pentene plus either ethylene or propylene, both valuable olefins, instead of consuming valuable propylenes. This results in a substantial reduction in net feed cost per unit 2-methyl-2 pentene produced.

2. The process described herein utilizes a fixed bed metathesis catalyst instead of a homogeneous catalyst for propylene dimerization that is used for the production of 2 methyl-2 pentene via other processes. This reduces operating costs because continuous catalyst feed is not required. It is noted the same fixed bed catalyst can be used in all of the metathesis reactions presented in this invention. Other 2-methyl-2-pentene processes like propylene dimerization, and the synthesis of isoprene from isobutylene and formaldehyde use homogeneous catalysts.

3. The overall metathesis selectivity to the sum of 2-methyl-2-pentene and ethylene and/or propylene can be at least 90%, or at least 95%.
4. The process utilizes mixed $C_4$ streams that are available as a by-product from cracking units. Conversion of $C_4$ olefins to ethylene or propylene and isoprene could potentially increase the value of the feed stream. Competitive processes involve the dehydrogenation of isoamylenes. If the $C_5$ stream from steam crackers is used as feed for the isoamylenes, this requires extensive separation of cyclopentadiene. Alternately isoamylenes can be produced by the metathesis of propylene and butenes involving high cost propylene as a feed.
5. Some embodiments of the process utilize an isomerization reactor that can convert 2-butene into 1-butene, making the process flexible to a variety of $C_4$ feed compositions.
6. The process can be integrated with olefins conversion technology (OCT) for the production of propylene and additional efficiencies can be realized:
    The process produces ethylene that can be used as part of the ethylene feed requirement in an OCT process producing propylene via a traditional metathesis reaction
    2-butene+ethylene→propylene+propylene
    The integrated process can send butene purges to the OCT process for additional reaction hence result in higher butene utilization
    In OCT, isobutylene will not react with ethylene via metathesis, and is therefore typically removed and sent to fuel as LPG. In the integrated process described herein, the isobutylene sent to LPG can be upgraded to higher value isoprene and ethylene or propylene
    Unwanted side reactions in OCT involve the reaction of 1-butene with 2-butene to produce propylene and 2-pentene. The 2-pentene byproduct from OCT can be utilized as feed for the production of 2-methyl-2 pentene
    The overhead light gases (ethylene and or propylene) can be recovered in the OCT fractionation train
    Integration allows the common use of regeneration and treatment facilities for the process since the catalysts are similar
7. Recovery of 2-methyl-2-pentene from cracking effluent results in small volumes of product, which would limit the production capacity for isoprene. Processes that are intended to produce 2-methyl-2-pentene result in higher volumes and concentrations.

The process is particularly useful for mixed $C_4$ feed streams containing 5-50 wt % or 10-30 wt % 1-butene, 5-50 wt % or 10-30 wt % 2-butene, 5-70 wt % or 10-60 wt % isobutylene and 0-25 wt % butane, based on 100 wt % of 1-butene, 2-butene, isobutylene and butane. Small quantities of butadiene, C3 compounds and C5 compounds may be present. In one embodiment, the feed stream has 0.1-0.3 parts of butadiene, 0-1 parts of C3 compounds, and 0-1 parts C5 compounds based on 100 parts in the feed stream.

The process described herein provides for 2-methyl-2-pentene actual yields of at least 30 wt %, or at least 40 wt % or at least 50 wt % based upon the $C_4$ olefin content of fresh feed. In some cases, the actual yield of 2-methyl-2pentene is 30-70 wt %, or 40-70 wt % or 50-70 wt %. Furthermore, actual yields of at least 10 wt %, or at least 20 wt % or at least 30 wt % propylene can be obtained. Actual yields of at least 5 wt %, or at least 10 wt %, or at least 20 wt % ethylene can be obtained. The ethylene and propylene can be used in certain embodiments of the process and/or can be removed as products.

The following Examples include several cases that have differing selectivities and conversions dependent upon feed composition. In integration with OCT, selectivity to propylene allows for recovery of propylene as valuable product.

EXAMPLES 1-4

Four processes for the production of 2-methyl-2-pentene from the metathesis reactions of $C_4$ olefins were simulated in Aspentech HYSYS. Each process was simulated with a typical steam cracker raffinate I feed blend of 50% wt. isobutylene, 25% wt. 1-butene, and 25% wt. 2-butene. The 2-methyl-2-pentene obtained is then used to produce isoprene. Raffinate I is defined as a mixed $C_4$ feed from which the butadiene has been removed. The butadiene can be removed either via selective hydrogenation or by solvent extraction. In order to be processed in a metathesis reactor, the butadiene should be removed to low levels. Raffinate I comprises a mixture of isobutane, isobutylene, 1-butene, c/t 2-butene and normal butane. The stream compositions used in the examples are based upon a pure olefin feed (no isobutane or normal butane paraffins). These compositions are in no way limiting and are used to illustrate the invention. In actual practice, the removal of paraffins from these streams is accomplished by additional fractionation and or purging from the reaction loops as the concentration of paraffins build up in recycles since the paraffins do not react over metathesis catalysts.

Example 1

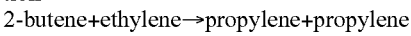

Production of Isoprene and Ethylene from 2-Methyl-2-Pentene Obtained by Catalytic Distillation-Deisobutylenization (CD-DIB) and Metathesis Reaction of Isobutylene and 1-Butene with Isomerization Loop Referring first to FIG. 1, the overall process for producing isoprene from mixed $C_4$ streams is designated as 100. The overall process includes a metathesis process 101 to form 2-methyl-2-pentene, and a pyrolysis and separation process 103 to produce isoprene.

Fresh raffinate I in stream 102 containing 50% wt. isobutylene, 25% wt. 1-butene, and 25% wt. 2-butene was catalytically distilled in tower 104 to separate isobutylene in top stream 106 from the n-butenes in bottoms stream 108. Catalytic distillation in this service utilizes a hydroisomerization catalyst within the distillation structures to allow for the isomerization of 1-butene to 2-butene as the fractionation proceeds. In the absence of this isomerization function, portions of the 1-butene and 2-butene in the feed would track overhead and be admixed with the overhead isobutylene product. This is done to minimize the 2-butene in the overhead isobutylene product that will be directed to the metathesis reaction. Stream 108 comprises mainly 2-butene. Stream 108 was then combined with a recycle stream 110 as stream 112, which was sent to an isomerization reactor 114 where an equilibrium 2-butene to 1-butene ratio was maintained (approximately 3.5:1 at 350° C.). The reaction product stream 116 contained 1-butene and 2-butene, which were separated in a distillation tower 118. The bottoms stream containing 2-butene was the recycle stream 110, which was recycled back to the isomerization reactor 114. The top stream 120 containing 1-butene distilled from distillation tower 118 was mixed with the isobutylene-containing top stream 106 from tower 104 and a recycle stream 122 in stream 124. Stream 124 was sent to a metathesis reactor 126 where the following metathesis reactions proceeded to equilibrium:

isobutylene+1-butene⇌ethylene+2-methyl-2-pentene isobutylene+isobutylene⇌ethylene+2,3-dimethyl-2-butene 1-butene+1-butene⇌ethylene+3-hexene The reactor effluent 128 contained 12% wt. unreacted 1-butene and 43% wt. unreacted isobutylene, with 25% wt. 2-methyl-2-pentene, 9% wt. ethylene, 6% wt. 2,3-dimethyl-2-butene, and 2% wt. 3-hexene. The reactor effluent stream 128 was sent to a distillation column 130 where ethylene was removed as a product in top stream 132. The bottoms liquid stream 134 containing $C_{3+}$ was sent to a distillation column 136 where $C_3$s, 3-hexene and unreacted isobutylene and 1-butene were removed in distillate stream 138, and bottoms stream 140 was a mixture of 2-methyl-2-pentene and 2,3-dimethyl-2-butene. This bottom stream 140 was sent to a distillation column 142 where the desired product 2-methyl-2-pentene was collected as a distillate stream 144. The bottoms stream 146 containing byproduct 2,3-dimethyl-2-butene was combined with distillate stream 138 from distillation column 136 to form recycle stream 122, which became part of stream 124 that was fed to the metathesis reactor 126. The 2,3-dimethyl-2-butene and 3-hexene in this recycle stream inhibited the byproduct forming side reactions and promoted the selectivity to the desired products. Overall performance data, i.e. overall feed conversion and product selectivity of the entire process from inlet stream 102 to outlet stream 144 on FIG. 1, is shown on Table 1 below. It is noted that "per pass" selectivity or conversion refers the performance of a particular reactor or unit, in this case reactor 126. "Overall" and "per pass" performance (conversion in particular) can differ depending on the arrangement of recycle streams inside the process.)

The remainder of the process to obtain isoprene was not simulated but illustrates the production of isoprene from stream 144, which contains a high concentration of 2-methyl-2-pentene. As indicated above, the pyrolysis and separation process is designated as 103. Distillate stream 144 is combined with recycle stream 148 to form stream 150, which is a 2-methyl-2-pentene rich stream. Stream 150 is fed to a thermal cracking furnace 152 where it is converted to a range of hydrocarbons, mainly isoprene, methane, and isobutylene. The furnace effluent stream 154 is sent to a distillation column 156 where methane and light gases including $C_4$ hydrocarbons are removed as distillate stream 158. Bottom stream 160 containing isoprene and cyclopentadiene is fed to vessel 161 where it is heated to 100° C., causing the cyclopentadiene to dimerize to dicyclopentadiene. Effluent stream 162 from vessel 161 is sent to distillation column 163 where $C_5$ hydrocarbons are taken overhead as stream 164. Dicyclopentadiene and $C_{6+}$ hydrocarbons are removed from the column in bottom stream 165. This stream optionally can be separated further in column 159 to collect dicyclopentadiene in stream 167 while recycling the remaining $C_{6+}$ hydrocarbons in stream 148 to the cracking furnace 152, or the entire stream 165 can be recycled as stream 148.

Stream 164 containing isoprene is fed to an extractive distillation vessel 166 where it is contacted with solvent from stream 169. Paraffins and mono-olefins leave the vessel overhead as stream 168, while the solvent and extract stream 170 are fed to the solvent stripping column 172. From this column, solvent stream 176 is recycled to the extractive distillation vessel 166 as part of stream 169 or is fed to a solvent regeneration system (not shown). Stream 174 containing isoprene and $C_5$ hydrocarbons is fed to a water washing column 178. Water stream 180 contacts the hydrocarbons and removes trace amounts of solvent as bottom stream 182. This stream is sent to distillation column 184 where solvent is separated as stream 186 and recycled to extractive distillation vessel 166 as part of stream 169. Water stream 180 is recycled to column 178.

The isoprene and $C_5$ hydrocarbon stream 181 leaves water washing column 178 as distillate and is fed to distillation column 188. Alkynes stream 190 is separated as distillate in distillation column 188, and bottoms stream 192 containing isoprene is fed to distillation column 194. Isoprene product stream 196 is collected as distillate and bottom stream 198 containing piperylenes is taken from the column bottom.

Using the above-described pyrolysis and separation process, using a purified 2-methyl-2-pentene feed to the thermal cracking furnace containing 96.7 wt % 2-methyl-2-pentene and 1.8 wt % 2,3-methyl-2-butene, at least 60 kg of isoprene can be obtained for every 100 kg of $C_4$ olefin feed. Based on the $C_4$ olefin content of the initial feed stream, 60 wt % of the feed is converted to isoprene, <1 wt % of the feed is converted to propylene, and 25 wt % of the feed is converted to ethylene.

It is noted that a variety of other separation processes can be used in place of the illustrated separation process to obtain the isoprene product. In general, the fractionation process involves multiple distillation columns and optionally include solvent extraction and/or extractive distillation.

Example 2

Production of Isoprene and Propylene from 2-Methyl-2-Pentene Obtained by a Metathesis Reaction of Isobutylene and 1-Butene, Combined with a Metathesis Reaction of Ethylene and 2-Butene to Produce Propylene Example 2 illustrates a process in which propylene is produced and the normal butene isomerization step and catalytic distillation of Example 1 are eliminated, thus saving cost and processing steps for the production of 2-methyl-2-pentene. Furthermore, the process of Example 2 produces a valuable propylene product.

Figure 2:
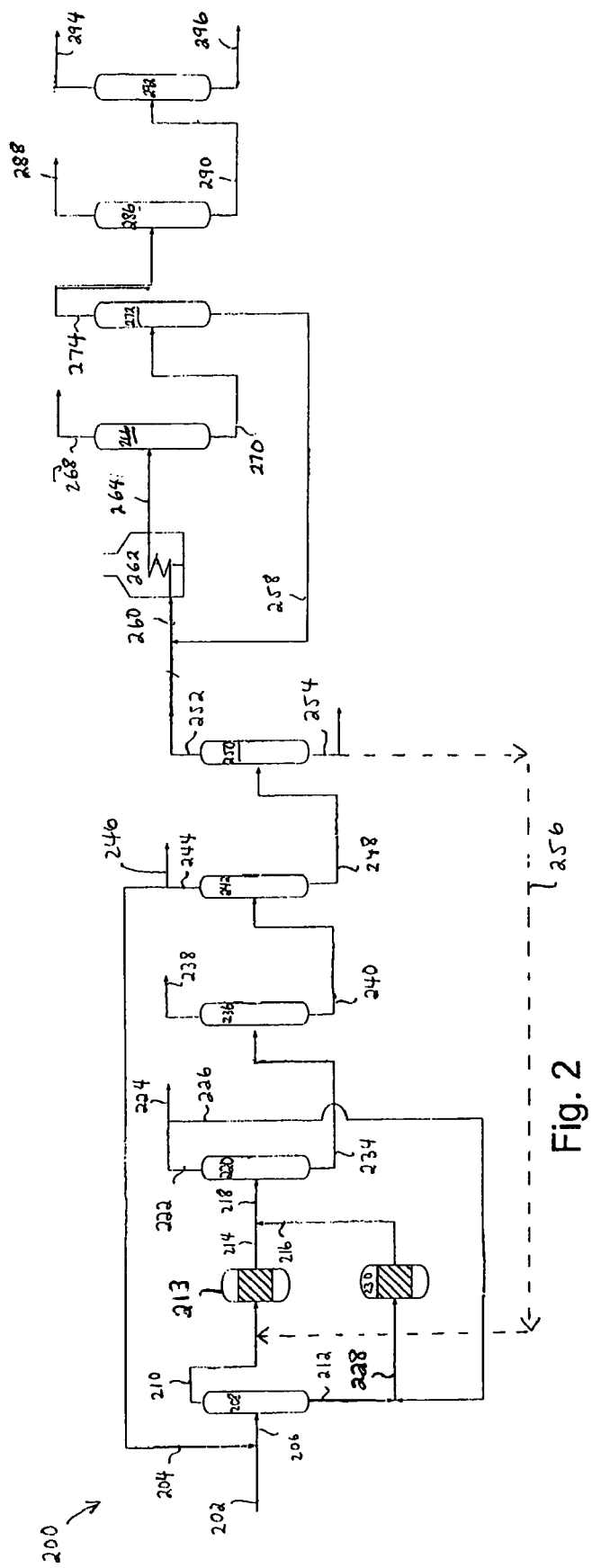
FIG. 2 is a flow sheet according to a second process and system described below.

Referring to FIG. 2, a process for producing isoprene from butenes is designated as 200. Fresh raffinate I in feed stream 202 containing 50% wt. isobutylene, 25% wt. 1-butene, and 25% wt. 2-butene was mixed with recycle stream 204 containing 81% wt. isobutylene, 9.5% wt. 1-butene, and 8.5% wt. 2-butene in a ratio of 1.5 kg of recycle for each kg of fresh feed. The combined $C_4$ stream 206 was distilled in a conventional distillation tower 208 to separate isobutylene and 1-butene in distillate stream 210 from 2-butene in bottoms stream 212. The distillate stream 210, containing 81% wt. isobutylene and 19% wt. 1-butene, was sent to a metathesis reactor 213 where the following reactions proceeded to equilibrium:

isobutylene+1-butene⇌ethylene+2-methyl-2-pentene isobutylene+isobutylene⇌ethylene+2,3-dimethyl-2-butene 1-butene+1-butene⇌ethylene+3-hexene The operating parameters of tower 208 controlled the concentration of 2-butene in the feed to the metathesis reactor 213. The quantity of 2-butene in the overhead stream 210 was purposely limited, but since the tower did not contain catalyst as in Example 1, some 2-butene was passed overhead. The majority of the 2-butene was removed from tower 208 as bottoms stream 212.

The presence of 2-butene in the feed to reactor 213 led to the equilibrium reactions of 2-butene with 1-butene and isobutylene:

2-butene+1-butene⇌propylene+2-pentene
2-pentene+isobutylene⇌propylene+2-methyl-2-pentene
2-butene+isobutylene⇌propylene+2-methyl-2-butene
2-methyl-2-butene+1-butene⇌2-methyl-2-pentene+propylene
2-pentene+isobutylene⇌propylene+2-methyl-2-pentene The reactor effluent in stream 214 contained 57% wt. unreacted isobutylene and 7% wt. unreacted 1-butene, which corresponded to a total feed conversion of approximately 37% mol. per pass. The metathesis reactor effluent stream 214 also contained 17% wt. 2-methyl-2-pentene, 9% wt. ethylene, 10% wt. 2,3-dimethyl-2-butene, and 0.5% wt. 3-hexene. The metathesis reactor effluent stream 214 was combined with a second metathesis effluent stream 216 to form stream 218. Stream 218 was sent to a distillation column 220 where ethylene was taken overhead in distillate stream 222. Part of the distillate stream 222 was collected as product in ethylene stream 224 while the rest, in recycle stream 226, was combined with 2-butene-containing bottoms stream 212, forming stream 228. Stream 228 was fed to a second metathesis reactor 230. Stream 228 had a molar composition of 66% ethylene and 33% 2-butene, a 2:1 ethylene-to-butene ratio. In the second metathesis reactor 230, the primary reaction proceeded to equilibrium:

ethylene+2-butene⇌propylene+propylene

The effluent in stream 216 from reactor 230 contained 16% wt. 2-butene (67% mol. conversion), 32% wt. ethylene, and 50% propylene product. Stream 216 was combined with stream 214 to form stream 218, which, as indicated above, was fed to the distillation column 220. The bottoms stream 234 from the distillation column 220 was sent to a distillation column 236 where propylene product was removed as distillate stream 238. The propylene stream 238 represents a valuable olefin product compared to prior known processes in which propylene is used as feed to produce 2-methyl-2-pentene via dimerization.

The bottoms stream 240 from distillation column 236 was sent to a distillation column tower 242, where the isobutylene-rich C$_4$ stream was removed as distillate stream 244. The distillate stream 244 was divided into recycle stream 204, which was mixed with feed stream 202, and an optional purge stream 246. The bottoms stream 248 from tower 242 contained 62% wt. of the desired 2-methyl-2-pentene product and 19 wt. % of 2,3-dimethyl-2-butene byproduct. These two components were separated from each other in distillation tower 250. 2-methyl-2-pentene was removed in top stream 252 and 2,3-dimethyl-2-butene was removed in bottoms stream 254. With a total feed conversion of 99.89%, the major products from the process were 37% wt. propylene, 35% wt. 2-methyl-2-pentene, 20% 2,3-dimethyl-2-butene, 6% ethylene, and 1% 3-hexene.

The remainder of the process to obtain isoprene was not simulated but illustrates a process for the production of isoprene from the 2-methyl-2-pentene in stream 252. It is noted that the multi-stage distillation process shown in FIG. 2 can be substituted by the extractive distillation process described in connection with FIG. 1. Furthermore, other processes involving fractionation with or without extraction can be used in place of the processes shown in FIGS. 1 and 2.

Stream 252 is combined with recycle stream 258 to form stream 260. Stream 260 is sent to a thermal cracking furnace 262 where it is converted to a range of hydrocarbons, mainly isoprene, methane and isobutylene. The furnace effluent stream 264 is sent to a distillation column 266, from which a methane distillate stream 268 is removed. In many cases, this stream becomes the fuel required for process heat. The bottoms stream 270 is sent to a distillation column 272. Crude isoprene distillate is removed from the column 272 in stream 274. The bottoms stream 258 is returned to the furnace 262 as part of stream 260. The isoprene distillate stream 274 is fed to a distillation tower 286. 2-methyl-1-butene is removed in distillate stream 288 and isoprene is removed in bottoms stream 290. The bottoms stream 290 is fed to a distillation column 292. High purity isoprene is removed as distillate stream 294 and 2-methyl-2-butene is removed in bottoms stream 296.

Using the pyrolysis and separation process of FIG. 2, when the feed to the thermal cracking furnace is a purified 2-methyl-2-pentene stream containing 96.7 wt % 2-methyl-2-pentene and 1.8 wt % 2,3-methyl-2-butene, at least 28 kg of isoprene can be obtained for every 100 kg of C$_4$ olefin feed. Based on the C$_4$ olefin content of the initial feed stream, 28 wt % of the feed is converted to isoprene, 37 wt % of the feed is converted to propylene, and 7 wt % of the feed is converted to ethylene. The actual isoprene yield is 50-65 wt. % based on the 2-methyl-2-pentene content of stream 144.

As an alternative to collecting the 2,3-dimethyl-2-butene from the bottom of distillation tower 250, all or a portion of stream 254 can be recycled in stream 256 to the metathesis reactor 213 to inhibit the reaction of isobutylene with itself. However, this requires a larger purge of isobutylene as it builds up in the C$_4$ recycle loop. Buildup of isobutylene occurs as the conversion of 1-butene in the metathesis reactor increases to 90% mol. per pass, while overall reactor C$_4$ conversion drops to 10% mol. per pass. Because there are negligible increases in the desired product yields, this is essentially a trade off between 2,3-dimethyl-2-butene for isobutylene in the purge streams 244 or 254 at the cost of a much higher recycle ratio. As the ratio of isobutylene to 1-butene in the fresh feed approaches 1:1 (rather than 2:1 in this example), recycling stream 254 to reactor 213 becomes more beneficial. While it is unlikely that this alternative would be used with the feed composition exemplified herein, it may useful with other feed compositions, such as a feed containing a 1:1 ratio of isobutylene to 1-butene, because this recycle stream would improve selectivity to 2-methyl-2-pentene.

Example 3

Production of Isoprene and Propylene from 2-Methyl-2-Pentene Obtained by Metathesis of 2-Butene and Ethylene Followed by Metathesis of Isobutylene and 1-Butene Example 3 is a variation of the configuration used in Example 2. While Example 2 utilized a metathesis reactor for the synthesis of 2-methyl-2-pentene from isobutylene and 1-butene in "parallel" to a metathesis reactor producing propylene from 2-butene and ethylene, Example 3 arranged these processes in "series."

Figure 3:
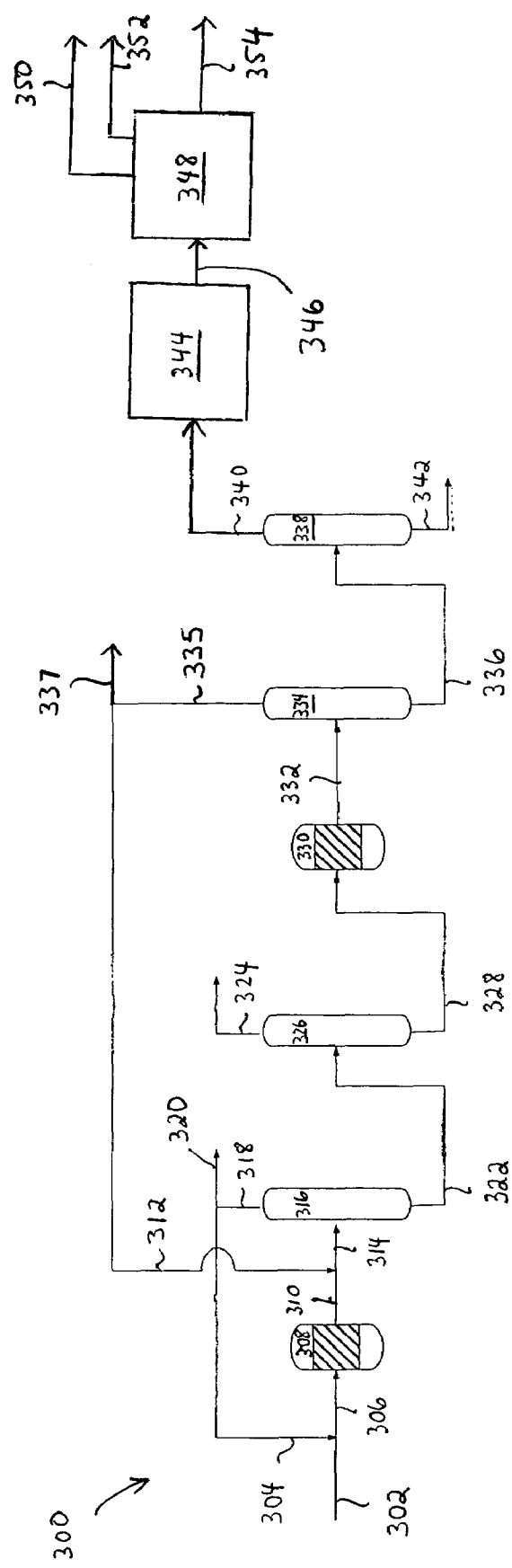
FIG. 3 is a flow sheet according to a third embodiment described below.

The overall process of Example 3 is shown in FIG. 3 and is designated as 300. Fresh raffinate I in stream 302 containing 50% wt. isobutylene, 25% wt. 1-butene, and 25% wt. 2-butene was mixed with ethylene stream 304 to form feed stream 306. The ratio of fresh C$_4$ in stream 302 to recycle C$_2$ in stream 304 was 2.0. Stream 306 was fed to a metathesis reactor 308 in which the primary reaction proceeded to equilibrium:

ethylene+2-butene⇌propylene+propylene

It is noted that the presence of ethylene inhibited the reaction of either isobutylene or 1-butene with itself and further, neither isobutylene nor 1-butene will react with ethylene. The reactor effluent stream 310 contained 2% wt. 2-butene, 32% wt. ethylene, 27% wt. isobutylene, 12% wt. 1-butene, and 19% wt. propylene product. The reactor effluent stream 310 also contained 4% wt. 2-methyl-2-pentene, 1.6% wt. 2-methyl-2-butene, 1.4% wt. 2-pentene, 0.6% wt. 2,3-dimethyl-2-butene, and 0.5% wt. 3-hexene from the reactions of isobutylene and 1-butene.

The reactor effluent stream 310 was mixed with a recycle stream 312 containing primarily ethylene (9.4% wt.), isobutylene (71% wt.) and 1-butene (8% wt.) to form stream 314. Stream 314 was fed to distillation tower 316 and was fractionated to form a top stream 318 containing ethylene, about 90% of which was recycled to the metathesis reactor 308 in stream 304 for propylene production. The other 10% was collected as ethylene product in stream 320. The bottoms stream 322 from distillation column 316 contained 16% wt. propylene, which was collected as a distillate in top stream 324 from distillation column 326. The propylene is a valuable olefin product. The bottoms product from distillation column 326 (stream 328), containing 72% wt. isobutylene, 15% wt. 1-butene, and 13% wt. 2-butene plus C$_5$+ olefins was fed to a metathesis reactor 330 where the following reactions proceed to equilibrium:

isobutylene+1-butene⇌ethylene+2-methyl-2-pentene
isobutylene+2-pentene⇌propylene+2-methyl-2-pentene
isobutylene+isobutylene⇌ethylene+2,3-dimethyl-2-butene
1-butene+1-butene⇌ethylene+3-hexene The reactor effluent stream 332 contained 50% wt. unreacted isobutylene and 6% wt. unreacted 1-butene, 18% wt. 2-methyl-2-pentene, 10% wt. 2,3-dimethyl-2-butene, 7% wt. ethylene, 4% wt. propylene, and 3% wt. 2-methyl-2-butene. The reactor effluent stream 332 was sent to tower 334 where 2-methyl-2-pentene and 2,3-dimethyl-2-butene were separated out in the bottoms stream 336. The ethylene, propylene, C$_4$'s, and C$_5$'s were collected as distillate in stream 335 and recycled in stream 312 to tower 316 where they were further separated as previously discussed. A small purge from stream 335, shown as 337 on FIG. 3, is necessary to remove any paraffin from the system from building up. The 2-methyl-2-pentene and 2,3-dimethyl-2-butene from the bottom of tower 334 in stream 336 were sent for further separation in tower 338, where the 2-methyl-2-pentene product was removed as a distillate in stream 340 and 2,3-dimethyl-2-butene was removed as bottoms stream 342.

The remainder of the process to obtain isoprene was not simulated but illustrates the production of isoprene from stream 340, which contains a high concentration of 2-methyl-2-pentene. The 2-methyl-2-pentene stream 340 undergoes pyrolysis at 344. The cracked stream 346 is subjected to a separation process at 348 to isolate isoprene at a desired purity level. Typically the separation process involves multistage distillation for the removal of lighter materials, for example methane and lights C$_4$s, in one or more separate streams, shown as 350 in FIG. 3, and heavier by-products in stream 352 in order to provide an isoprene product stream 354 of the desired purity. Extraction also can be used, either as part of an extractive distillation process or as a separate step. The pyrolysis and separation processes described in Examples 1 and 2 are suitable, as well as other processes that will achieve the desired purity of the isoprene product stream. The actual isoprene yield is 50-65 wt. % based on the 2-methyl-2-pentene content of stream 144.

It is noted that although Examples 2 and 3 were similar in overall product composition, Example 3 required one fewer distillation towers than Example 2 because there was no separation of isobutylene from 2-butene and 1-butene before entering the first reactor. In both of these cases, a small purge stream was required to balance compositions as well a remove any small amounts of paraffins that entered with the fresh feeds.

Example 4

Figure 4:
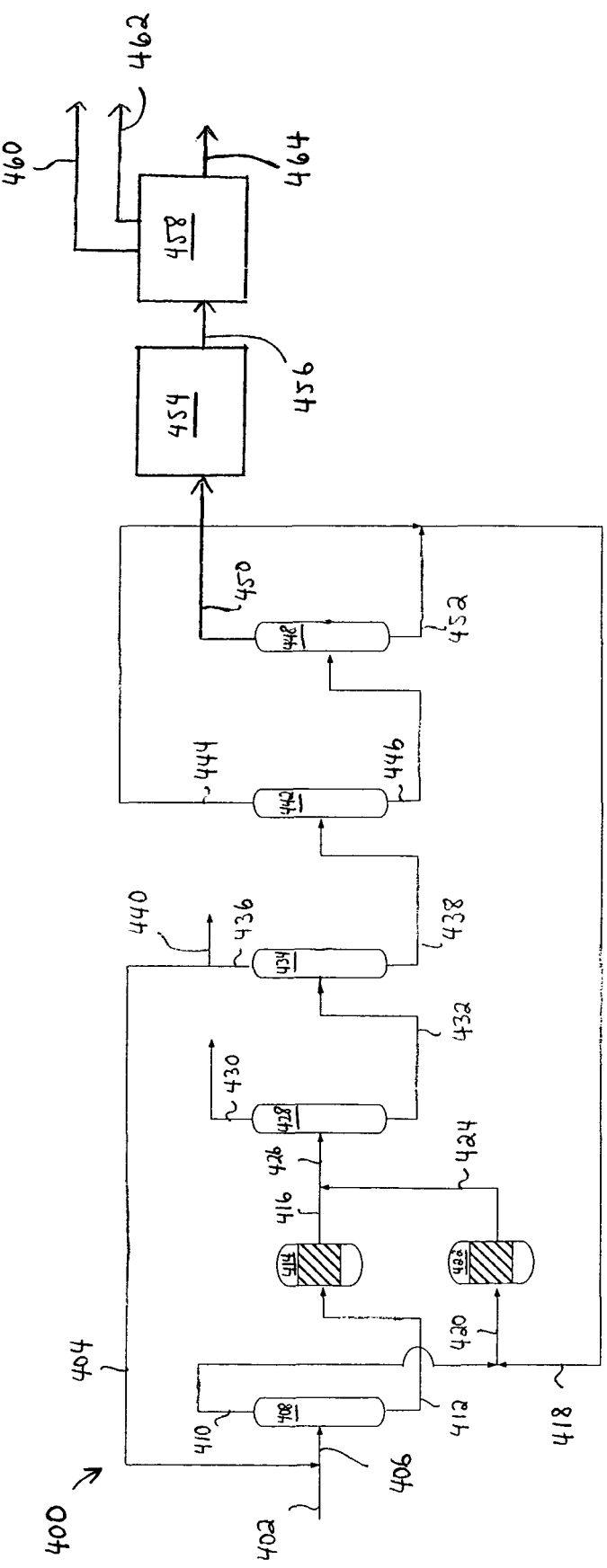
FIG. 4 is a flow sheet according to a fourth embodiment.

Production of Isoprene and Propylene from 2-Methyl-2-Pentene Obtained by Metathesis of Isobutylene and 2-Pentene The overall process of Example 4 is shown in FIG. 4 and is generally designated as 400. Fresh raffinate I in stream 402 containing 50% wt. isobutylene, 25% wt. 1-butene, and 25% wt. 2-butene was mixed with a recycle stream 404 containing 68% isobutylene, 2% wt. 1-butene and 30% wt. 2-butene to form feed stream 406. The ratio of recycle feed in stream 404 to fresh feed in stream 402 is 2.1. Stream 406 was fed to a distillation tower 408 where isobutylene was removed as a distillate in stream 410. This tower differs from previous cases in that the overhead product is relatively pure isobutylene and the majority of the normal butenes are taken as bottoms product. The n-butenes bottom stream 412 comprising butene-1 and butene-2 was sent to a metathesis reactor 414 where the following metathesis reactions proceeded to equilibrium:

1-butene+2-butene⇌propylene+2-pentene
1-butene+1-butene⇌ethylene+3-hexene
ethylene+2-butene⇌propylene+propylene The reactor 414 effluent stream 416 contained 67% wt. unreacted 2-butene and 2% wt. unreacted 1-butene, 18% wt. 2-pentene, 11% wt. propylene, and 1% wt. 3-hexene.

The isobutylene distillate in stream 410 from tower 408 was combined with a recycle stream 418 containing 2-pentene and 2-methyl-2-butene to form a feed stream 420, which was fed to a second metathesis reactor 422. The feed stream 420 also contained 37% wt. 2,3-dimethyl-2-butene recycled from the distillation sequence (described below) as part of stream 418 in order to inhibit the reaction of isobutylene with itself. The following reactions proceeded to equilibrium in the metathesis reactor 422:

2-pentene+isobutylene⇌propylene+2-methyl-2-pentene
2-pentene+isobutylene⇌1-butene+2-methyl-2-butene
isobutylene+isobutylene⇌ethylene+2,3-methyl-2-butene
2-pentene+2-pentene⇌2-butene+3-hexene
2-methyl-2-butene+isobutylene⇌propylene+2,3-methyl-2-butene
2-methyl-2-butene+2-pentene⇌2-methyl-2-pentene+2-butene The effluent stream 424 from the metathesis reactor 422 contained 42% wt. unreacted isobutylene, 9% wt. 2-methyl-2-pentene, 7% wt. 2-methyl-2-butene, 37% wt. 2,3-dimethyl-2-butene, 2% wt. propylene, and 1% wt. ethylene. The reactor effluent stream 416 and the reactor effluent stream 424 were combined to form stream 426, which was fed to a distillation column 428. Propylene and ethylene were removed from the distillation column 428 in a distillate stream 430, and the bottoms stream 432 contained the C$_4$s, C$_5$s and C$_6$ olefins. The bottoms stream 432 was fed to a distillation column 434 in which the unreacted C$_4$'s are removed as a distillate stream 436 and the C$_5$'s and C$_6$'s are removed in the bottoms stream 438. The distillate stream 436 was separated into a purge stream 440 and a recycle stream 404, which is combined with fresh feed in stream 402. The bottoms stream 438 was fed to a distillation column 442 in which 2-pentene and 2-methyl-2-butene were removed in a distillate stream 444 and the branched $C_6$'s were removed in a bottoms stream 446. The bottoms stream 446 was fed to a distillation column 448 in which 2-methyl-2-pentene was removed in a distillate stream 450 and 2,3-dimethyl-2-butene was removed in a bottoms stream 452 and combined with stream 444 to form recycle stream 418. Recycle stream 418 containing 2,3-dimethyl-2-butene was combined with stream 410 and fed to the second metathesis reactor 422 in order to inhibit the reaction of isobutylene with itself.

The remainder of the process to obtain isoprene was not simulated but illustrates the production of isoprene from stream 450, which contains a high concentration of 2-methyl-2-pentene. The 2-methyl-2-pentene stream 450 undergoes pyrolysis at 454. The cracked stream 456 is subjected to a separation process at 458 to isolate isoprene at a desired purity level. Typically the separation process involves multi-stage distillation for the removal of lighter materials, for example methane and lights $C_4$s, in one or more separate streams shown as 460 FIG. 4, and heavier by-products in stream 462 in order to provide an isoprene product stream 464 of the desired purity. Extraction also can be used, either as part of an extractive distillation process or as a separate step. The pyrolysis and separation processes described in Examples 1 and 2 are suitable, as well as other processes that will achieve the desired purity of the isoprene product stream. The actual isoprene yield is 50-65 wt. % based on the 2-methyl-2-pentene content of stream 144.

The results of the four simulations are summarized in Table 1 below in terms of overall molar feed conversion, weight selectivity and yield to the desired 2-methyl-2-pentene product. The selectivity and yield of ethylene and propylene byproducts also is shown.

TABLE 1

| | Example 1 | Example 2 | Example 3 | Example 4 |
|---|---|---|---|---|
| Fresh Feed Composition (wt. %) | | | | |
| Isobutylene | 50% | 50% | 50% | 50% |
| 1-butene | 25% | 25% | 25% | 25% |
| 2-butene | 25% | 25% | 25% | 25% |
| Overall Feed Conversion (mol. %) | 100.00% | 99.89% | 99.94% | 63.01% |
| 2M2P Selectivity (wt. %) | 74.83% | 34.97% | 35.13% | 58.04% |
| 2M2P Yield (wt. %) | 74.83% | 34.93% | 35.11% | 36.54% |
| $C_3$ Selectivity (wt. %) | 0.04% | 37.15% | 37.39% | 32.63% |
| $C_3$ Yield (wt. %) | 0.04% | 37.11% | 37.37% | 20.54% |
| $C_2$ Selectivity (wt. %) | 24.97% | 6.48% | 6.33% | 8.81% |
| $C_2$ Yield (wt. %) | 24.97% | 6.48% | 6.32% | 5.55% |
| Overall 2M2P + $C_3$ + $C_2$ Product Selectivity | 99.84% | 78.6% | 78.85% | 99.48% |

The process of Example 1 is particularly useful when no propylene product is desired and the quantity of 2-methyl-2-pentene (for isoprene) from a given quantity of $C_4$ olefins is to be maximized. The process of Example 2 is advantageous when the quantity of C olefins is in excess of the quantity required to produce the desired 2-methyl-2-pentene (for isoprene). Thus valuable propylene is produced as a co-product. The Example 3 process is a variation of case 2 with a different fractionation/reaction sequence. The amounts of each product obtained are comparable to the results of Example 2. It is noted that Example 3 is useful for a wide variety of $C_4$ feed compositions. The process of Example 4 illustrates a processing sequence where intermediate production of both 2-methyl-2-pentene and propylene is desired. The sequence may fit certain production capacity scenarios.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A process comprising:
    obtaining a mixed $C_4$ stream comprising isobutylene, 1-butene and 2-butene,
    removing at least a portion of the 2-butene,
    isomerizing the removed portion of the 2-butene in an isomerization reactor to obtain additional 1-butene, and combining the additional 1-butene with the remainder of the mixed $C_4$ stream to form a mixed $C_4$ metathesis feed stream comprising isobutylene and 1-butene,
    reacting the mixed $C_4$ metathesis feed stream in a first metathesis reactor in the presence of a first metathesis catalyst under conditions sufficient to produce an intermediate product stream comprising at least 30 wt. % 2-methyl-2-pentene based upon the olefin content of fresh feed in the mixed $C_4$ metathesis feed stream, and at least one of ethylene and propylene,
    separating the 2-methyl-2-pentene,
    subjecting the separated 2-methyl-2-pentene to pyrolysis to produce a reaction product stream comprising isoprene, and
    separating the isoprene into an isoprene product stream using fractionation.

2. The process of claim 1, wherein the actual yield of 2-methyl-2-pentene prior to pyrolysis is 30-70 wt % based upon the $C_4$ olefin content of fresh feed.

3. The process of claim 2, wherein at least 50 wt % of the 1-butene in the mixed $C_4$ metathesis feed stream is obtained by isomerizing 2-butene in the isomerization reactor.

4. The process of claim 1, wherein 2-butene removed from the isomerization reactor is separated from the 1-butene and recycled to the isomerization reactor.

5. The process of claim 1, wherein the first metathesis reactor contains a fixed bed catalyst.

6. The process of claim 1, wherein separating the isoprene includes a combination of fractionation and extraction.

7. The process of claim 1, wherein the intermediate product stream contains at least 40 wt % 2-methyl-2-pentene based upon the olefin content of fresh feed.

8. The process of claim 1, wherein the isoprene is separated using extractive distillation.

9. A process comprising:
    obtaining a mixed $C_4$ stream comprising isobutylene, 1-butene and 2-butene,
    separating the mixed $C_4$ stream to form a 2-butene stream and a mixed $C_4$ metathesis feed stream comprising isobutylene and 1-butene,
    reacting the mixed $C_4$ metathesis feed stream in the presence of a first metathesis catalyst under conditions sufficient to produce an intermediate product stream comprising at least 30 wt. % 2-methyl-2-pentene based upon the olefin content of fresh feed in the mixed $C_4$ metathesis feed stream and at least one of ethylene and propylene,
    fractionating the intermediate product stream to form a 2-methyl-2-pentene stream and at least one of an ethylene stream and a propylene stream, subjecting the separated 2-methyl-2-pentene stream to pyrolysis to produce a reaction product stream comprising isoprene, and separating the isoprene to form an isoprene product stream using fractionation.

10. The process of claim 9, further comprising reacting the 2-butene stream and ethylene in a second metathesis reactor to produce propylene.

11. The process of claim 10, wherein the ethylene that is reacted with the 2-butene is obtained from the intermediate product stream.

12. The process of claim 10, wherein unreacted ethylene is recovered and recycled.

13. The process of claim 9, wherein the actual yield of 2-methyl-2-pentene prior to pyrolysis is 30-70 wt % based upon the $C_4$ olefin content of fresh feed.

14. The process of claim 9, wherein the intermediate product stream contains at least 40 wt % 2-methyl-2-pentene based upon the olefin content of fresh feed.

15. A process comprising:
obtaining a mixed $C_4$ stream comprising isobutylene, 1-butene and 2-butene, reacting the mixed $C_4$ stream and ethylene in a second metathesis reactor to obtain a metathesis product stream comprising ethylene, propylene, isobutylene and 1-butene, and removing at least a portion of the ethylene and propylene to form the mixed $C_4$ metathesis feed stream, reacting the mixed $C_4$ metathesis feed stream in a first metathesis reactor in the presence of a first metathesis catalyst under conditions sufficient to produce an intermediate product stream comprising at least 30 wt. % 2-methyl-2-pentene based upon the olefin content of fresh feed in the mixed $C_4$ metathesis feed stream, and at least one of ethylene and propylene, separating the 2-methyl-2-pentene, subjecting the separated 2-methyl-2-pentene to pyrolysis to produce a reaction product stream comprising isoprene, and separating the isoprene into an isoprene product stream using fractionation.

16. The process of claim 15, wherein the intermediate product stream contains at least 40 wt % 2-methyl-2-pentene based upon the olefin content of fresh feed.

* * * * *